United States Patent [19]
Petuch et al.

[11] Patent Number: 5,219,985
[45] Date of Patent: Jun. 15, 1993

[54] ANTIFUNGAL AGENT

[75] Inventors: Brian R. Petuch, Florence; Byron H. Arison, Watchung, both of N.J.

[73] Assignee: Merck & Co., Inc., Rahway, N.J.

[21] Appl. No.: 607,430

[22] Filed: Oct. 31, 1990

[51] Int. Cl.$^5$ .................. A61K 37/02; C07K 5/12; C07K 7/06
[52] U.S. Cl. ............................................. 530/317
[58] Field of Search ...................... 530/317; 514/19

[56] References Cited

U.S. PATENT DOCUMENTS 5,021,341  6/1991  Giacobbe et al. .................. 435/71.1

FOREIGN PATENT DOCUMENTS 0021685  1/1981  European Pat. Off. .
0086092  8/1983  European Pat. Off. .
0405997  2/1991  European Pat. Off. .

OTHER PUBLICATIONS

Schmatz, et al. Proc. Natl. Acad. Sci. USA 87 (15) 5950–4, 1990.

Primary Examiner—Merrell C. Cashion, Jr.
Assistant Examiner—S. G. Marshall
Attorney, Agent, or Firm—Alice O. Robertson; Raymond M. Speer

[57] ABSTRACT

A compound having the formula

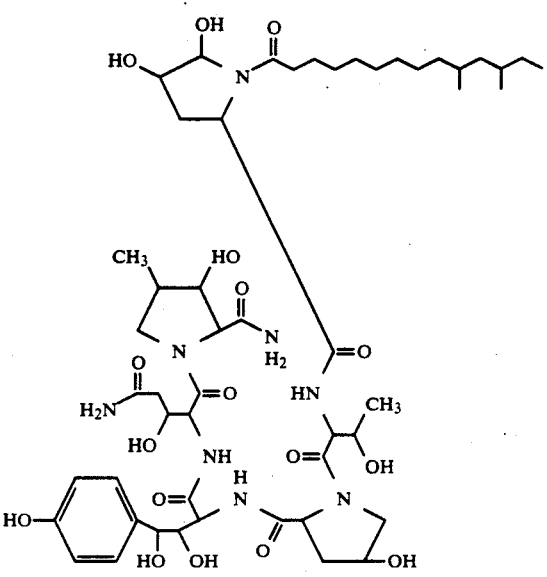

and a method of obtaining said compound is described. The compound has antifungal properties.

2 Claims, No Drawings

ANTIFUNGAL AGENT

BACKGROUND OF THE INVENTION

The present invention is concerned with an antifungal agent produced by microbial transformation a cyclohexapeptide compound with certain microorganisms.

DESCRIPTION OF THE INVENTION

According to the present invention it has been discovered that a biotransformation product having antifungal properties may be produced by biotransformation of a cyclohexapeptide compound employing certain bacterial organism.

The antifungal biotransformation product may be represented by the formula (I)

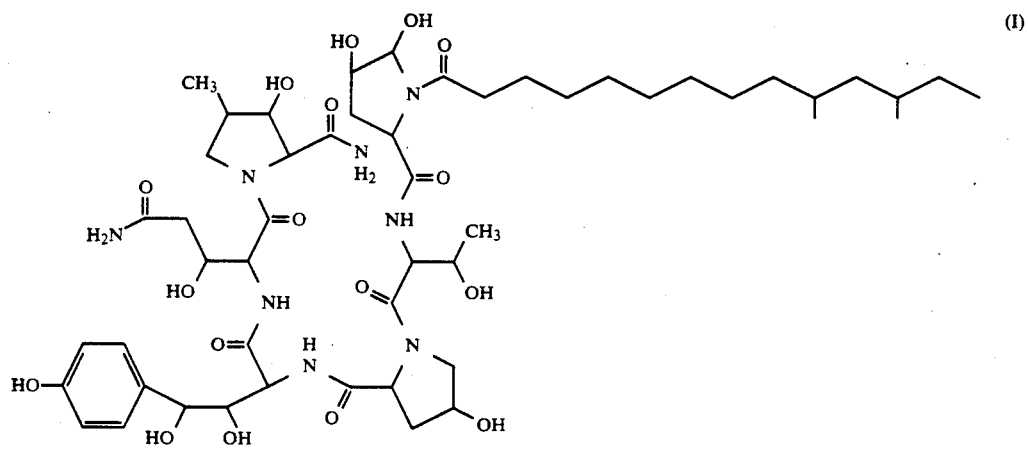

(I)

having SEQ ID No. 1.

The structure of the compound has been determined by detailed analyses of the spectral characteristics of the compound.

Mass Spectrum. An empirical formula of $C_{51}H_{82}N_8O_{17}$ was determined by high resolutions Fast Atom Bombardment (FAB) mass spectrometric measurement.

Nuclear Magnetic Resonance Spectra. $^{13}$C-NMR chemical shift obtained in $CD_3OD$ at 100 MHz are as follows: 176.56; 176.02; 175.02; 174.64; 174.13; 172.64; 171.97; 170.55; 158.32; 132.95; 129.61; 116.12; 88.78; 77.07; 76.75; 76.56; 75.45; 71.09; 70.85; 69.67; 68.85; 61.37; 60.73; 57.98; 57.16; 56.63; 55.53; 52.63; 45.92; 39.82; 38.82; 38.68; 38.05; 35.94; 34.85; 32.89; 31.23; 31.11; 30.72; 30.58; 30.42; 30.34; 28.03; 26.21; 20.72; 20.76; 19.70; 11.57; 11.10 ppm.

The compound is a white solid, soluble in organic solvents such as methanol, ethanol, 2-propanol, acetone, methyl ethyl ketone and the like.

Compound I has antifungal properties against many organisms and is particularly useful against organisms causing pathogenic mycotic infections such as *Candida albicans, Candida tropicalis* and *Candida parapsilosis*.

In addition to the particular usefulness of Compound I as a therapeutic agent in the treatment of mycotic infections, it is adapted to be employed wherever control of fungi is desired. Thus, it may be employed to control fungal species such as Aspergillus, Penicillium, Alternaria, Monilia, and Aureabasidium species which may be found on consumer articles; *Erisiphe polygoni, Alternaria solani,* and *Cochliobolus miyabeanus* which infect plants, *Rhizictonia solani* and *Fusarium solani,* which infect soil, *Lenzites trabea* which infect wood as well as other filamentous fungi and yeasts.

The compound of the present invention (Compound I) is produced by biotransformation of a cyclohexapeptide compound having the formula A SEQ ID NO. 2

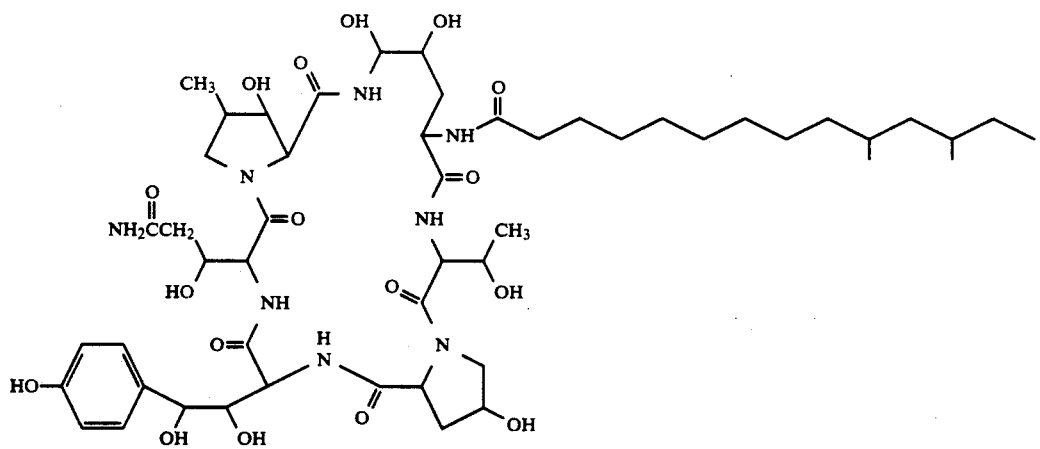

(A)

using a bacterial culture.

The bacteria especially useful have been found to be Bacillus, Pseudomonas and Arthrobacter species. Representative bacterial species are *Bacillus sphaericus* ATCC 7075, *Pseudomonas pseudoalcaligenes* ATCC 12815 and *Arthrobacter simplex* ATCC 6946, all available from the American Type Culture Collection at 12301 Parklawn Drive, Rockville, MD 20852. The cultures employed in the present biotransformation were from the Merck Culture Collection and derived by serial passage from the ATCC cultures. Their colonial and morphological properties are as follows:

Arthrobacter simplex

This culture MB255 in the Merck Culture Collection was derived by serial passage from ATCC 6946. Gram positive rods 0.57 μm diameter × 1.52-2.28 μm length. Culture exhibits a rod-coccus growth cycle with stationary cells occurring primarily in coccoid form. Growing cells occur as single rods and short chains of 2-3 cells and are motile. Obligately aerobic. Growth occurs at 28° and 37° C. on trypticase soy agar, trypticase soy agar supplemented with 5% sheep red blood cells, nutrient agar, Sabouraud's maltose agar. Slight growth on eosin methylene blue agar. No growth on MacConkey's agar. Growth also occurs in trypticase soy broth and fluid thioglycolate (at the surface only). On trypticase soy agar at 72 hours (28° C.) colonies are translucent, raised, have an entire edge and a glistening surface. Colony texture is butyrous. Culture exhibits α-hemolysis on sheep blood agar. Catalase negative, oxidase negative, nitrate is not reduced, $H_2S$ produced, acid is not produced from glucose, sucrose or lactose. These data compare favorably with the published description of *Arthrobacter simplex*.

Bacillus sphaericus var. fusiformis

This culture MB847 in the Merck Culture Collection was derived by serial passage from ATCC 7075. Gram positive, motile rods, 0.76 μm diameter × 1.8-2.7 μm length. Rapidly decolorizes. Cells occur singly and in short chains of 2-5 cells. Obligately aerobic. Growth occurs at 28° and 37° C. on trypticase soy agar, trypticase soy agar supplemented with 5% sheep red blood cells, nutrient agar, Sabouraud's maltose agar. Slight growth on eosin methylene blue agar. No growth on MacConkey's agar. Growth also occurs in trypticase soy broth and fluid thioglycolate (to a depth of 3.5 mm). On trypticase soy agar at 72 hours (28° C.) colonies are translucent, raised, have an entire edge. The surface tends to have a puckered appearance especially in larger colonies. Colony texture is butyrous. Culture exhibits β-hemolysis on sheep blood agar (72 hours). Catalase positive, oxidase positive, nitrate is not reduced, $H_2S$ produced, acid is not produced from glucose, sucrose or lactose. Parasporal bodies observed by phase microscopy, however, neither sporangial swelling nor free spores observed under the growth conditins used. These characteristics are consistent with the published description of *Bacillus sphaericus*. These data compare favorably with the published description of *Bacillus sphaericus*.

Pseudomonas pseudoalcaligenes

This strain MB1225 in the Merck Culture Collection was derived by serial passage from ATCC 12815. Gram negative, motile rod, 0.38-0.7 μm diameter × 1.14-1.9 μm length. No growth under anaerobic conditions. Cells occur singly or in pairs. Filaments rarely observed. Obligately aerobic. Growth occurs at 28° and 37° C. on trypticase soy agar, trypticase soy agar supplemented with 5% sheep red blood cells, nutrient agar, Sabouraud's maltose agar, eosin methylene blue agar and MacConkey's agar. Growth also occurs in trypicase soy broth and fluid thioglycolate. On trypticase soy agar at 72 hours (28° C.) colonies are translucent, raised and have an entire edge. Colonies have a butyrous texture and the surface glistens slightly. No hemolysis is observed on sheep blood agar (72 hours). Catalase positive, oxidase positive, nitrate is reduced to nitrate, $H_2S$ produced, acid is not produced from glucose, sucrose or lactose. These characteristics are consistent with the published characteristics of *Pseudomonas pseudoalcaligenes*.

The starting compound may be obtained by the cultivation of *Zalerion arboricola* ATCC 20868 and is the subject of U.S. Pat. No. 4,931,352, Jun. 5, 1990, and copending application Ser. No. 105,797, filed Oct. 7, 1987 now U.S. Pat. No. 4,968,608, Nov. 6, 1990.

Compound I may be obtained by cultivation of a culture of one of the foregoing bacterial species with cyclohexapeptide Compound A in a medium containing sources of carbon and nitrogen assimilable by the microorganism and also containing low levels of inorganic salts.

The sources of carbon include glycerol, sugars, starches and other carbohydrates or carbohydrate derivatives such as dextran, cerelose, as well as complex nutrients such as oat flour, soy flour, corn meal, millet, corn and the like. The exact quantity of the carbon source which is utilized in the medium will depend, in part, upon the other ingredients in the medium, but it is usually found that an amount of carbohydrate between 0.5 and 5 percent by weight of the medium is satisfactory. These carbon sources can be used individually or several such carbon sources may be combined in the same medium.

The sources of nitrogen include protein hydrolysates such as yeast hydrolysates, yeast autolysates, yeast cells, tomato paste, soybean meal, casein hydrolysates, yeast extracts, peptone, corn steep liquors, distillers solubles, cottonseed meal, meat extract, and the like. The various sources of nitrogen can be used alone or in combination in amounts ranging from 0.2 to 90 percent by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also, trace metals such as cobalt, manganese, iron, molybdenum, zinc, cadmium, and the like may be included.

Generally, seed cultures are first prepared and used to inoculate transformation cultures to obtain the desired transformation product. Components of representative seed and transformation cultures are given below. The media are made up in distilled water unless otherwise noted.

| Seed Medium A | g/l | Transformation Medium A | g/l |
|---|---|---|---|
| Dextrose | 1.0 | Glucose | 10.0 |
| Dextrin | 10.0 | "Hy-Case" SF* | 2.0 |
| Beef extract | 3.0 | Beef extract | 1.0 |

-continued

| | | | |
|---|---|---|---|
| "Ardamine" PH* | | Corn steep liquor | 3.0 |
| "NZ Amine" ** Type E | 5.0 | pH 7.0 | |
| $MgSO_4.7H_2O$ | 0.05 | | |
| $K_2HPO_4$ | 0.37 | | |
| pH 7.1 | | | |
| Add $CaCO_3$ 0.5 g/l | | | |

**Yeast autolysate, Yeast Products Inc.
**Casein hydrolysate; Sheffield Products Kraft, Inc.
*Casein hydrolysate Sheffield Products; "Hy-Case" Trademark of Dart and Kraft, Inc.

| Seed Medium B | g/l | Transformation Medium B | g/l |
|---|---|---|---|
| Glucose | 20 | Glucose | 50 |
| Soluble starch | 30 | Polypeptone | 5 |
| Soybean flour | 10 | Corn steep liquor | 20 |
| Corn steep liquor | 10 | NaCl | 3 |
| Polypeptone | 5.0 | $CaCO_3$ | 5 |
| NaCl | 3.0 | pH 7.0. | |
| $CaCO_3$ | 5.0 g | | |
| pH 7.0. | | | |

| Transformation Medium C | g/l | Transformation Medium D | g/l |
|---|---|---|---|
| Glucose | 1 | Cerelose | 30.0 |
| Peptone | 2 | Ammonium tartrate | 7.5 |
| Meat extract | 1 | Dipotassium phosphate | 2.0 |
| Yeast extract | Salts | 10.0 ml | |
| Corn steep liquor | 3 | Yeast extract | 1.0 |
| | pH 7.0 | | |

| Transformation Medium E | g/l | Salts | g/l |
|---|---|---|---|
| Sucrose | 10.0 g | Magnesium sulfate.$7H_2O$ | 25.00 |
| Tryptone medium (Difco) | 10.0 g | Ferrous sulfate.$7H_2O$ | 2.80 |
| $NaNO_3$ | 2.0 g | Manganous sulfate.$H_2O$ | 1.70 |
| $K_2HPO_4$ | 1.0 g | Sodium chloride | 0.60 |
| $MgSO_4.7H_2O$ | 0.5 g | Calcium chloride.$2H_2O$ | 0.10 |
| KCl | 0.5 g | Sodium molybdate.$2H_2O$ | 0.10 |
| $FeSO_4.7H_2O$ | 10.0 mg | Zinc sulfate.$7H_2O$ | 0.06 |
| pH 7 | | Hydrochloride acid, 0.1 M | 1.00 liters |
| $CaCO_3$ | 2.5 | | |

| Seed Medium F | g/l | Transformation Medium F | g/l |
|---|---|---|---|
| Glucose | 30.0 | Glycerol | 40.0 |
| Lactose | 10.0 | Cornstarch | 20.0 |
| Ammonium sulfate | 2.0 | Pharmamedia | 15.0 |
| Potassium phosphate monobasic | 0.5 | Washed brewers' yeast | 10.0 |
| Corn steep liquor | 30.0 ml | $MgSO_4.7H_2O$ | 0.5 |
| | $CaCl_2$ | 0.5 | |
| | | $ZnSO_4.7H_2O$ | 10.0 mg |

*deionized water

| Transformation Medium G | g/l | Transformation Medium H | g/l |
|---|---|---|---|
| Glucose | 10 g | Malt extract | 1.0 |
| Starch | 20 g | Beef extract | 1.0 |
| Peptone | 5 g | Yeast extract | 1.0 |
| Yeast extract | 5 g | Corn steep liquor | 1.0 ml |
| L-Asparagine | 3 g | Glucose | 5.0 |
| $CaCO_3$ | 4 g | deionized water | 1.0 liter |
| pH 7.4 | | pH adjusted to 5.5 with | |
| | 2 N HCl | | |

| Transformation Medium I | g/l | Transformation Medium J | g/l |
|---|---|---|---|
| Glucose | 10 | Corn steep (60% solids) | 20 |
| Corn Steep liquor | 10 | Glucose | 10 |
| Soy flour | 10 | | |
| Dry malt extract | 5 | | |
| $CaCO_3$ | 1 | | |
| NaCl | 5 | | |

*Tap water

| Seed Medium K | g/l | Transformation Medium K | g/l |
|---|---|---|---|
| Glucose | 20 | Glucose | 10.0 |
| Soybean meal | 5 | Corn steep liquor | 6.0 |
| Yeast extract | 5 | Potassium phosphate, monobasic | 3.0 |
| Sodium chloride | 5 | | |
| Potassium phosphate, dibasic | 5 | Calcium carbonate | 3.5 |
| | | Soybean oil | 2.2 ml |
| | | Yeast extract | 2.5 |

For producing the compounds of the present invention, a seed culture is first prepared from a preserved culture of the producing organism and thereafter grown in a suitable nutrient medium.

The seed culture may be prepared by inoculating an appropriate seed medium with cells taken from a preserved culture of a suitable bacterial species and incubating on a rotary shaker (220 rpm) at temperatures in the range of 25° C. to 30° C., preferably, 27° C. for a period of from about 18 to 25 hours, preferably, 24 hours.

The seed culture thus obtained is then used to inoculate a transformation culture medium to which has been added a solution of Compound A. The transformation medium is incubated at a temperature in the range 25° to 30° C., preferably 27° C. for from 18 to 25, preferably 24 hours.

After completion of the incubation the broth is filtered and extracted with a solvent having low miscibility in water. Suitable solvents include methyl ethyl ketone and ethyl acetate. The extract solution are combined and dried, then the dried solution evaporated to recover the transformation product, Compound I, as residue.

The product may be purified by high performance liquid chromatography (HPLC). Although various commercially available HPLC columns may be employed, the preferred column is Whatman "Partisil" with aqueous acetonitrile for developing.

The antifungal activity of Compound I against pathogenic fungi causing mycotic infections may be illustrated with assay results in a disk diffusion assay against Candida organisms employing yeast nitrogen base dextrose agar medium.

In carrying out the assay, Compound I was solubilized in 10 percent dimethyl sulfoxide (DMSO) supplemented with one drop of Tween 20. Twofold dilutions were made with a mixture of sterile distilled water containing 10 percent DMSO to obtain final drug concentrations of 128 to 0.06 μg/ml and assayed against strains of Candida and Cryptococcus. The inoculum was $1 \times 10^3$ cells/well.

The results in minimum fungicidal concentration are given below. Minimum fungicidal concentration μg/ml was defined as the lowest concentration of drug that totally prevented growth or permitted growth of no more than three colonies. The results were as follows:

| Organism | Compound I |
|---|---|
| *Candida Albicans* | |
| MY1055 | 4.0 |
| MY1585 | 2.0 |
| MY1208 | 4.0 |
| MY1028 | 4.0 |
| MY1750 | 4.0 |
| MY1783 | 2.0 |
| *Candida tropicals* | |
| MY1012 | 2.0 |
| *Candida parapsilosis* | |
| MY1009 | 32.0 |
| MY1010 | 32.0 |

The antifungal properties of the present invention may be effectively utilized by administering an antifungal amount of Compound I to the area, object or subject on or in which control of fungi is desired. The amount of Compound I to be employed depends on the particular fungal organism to be controlled and the particular environment in which it is to be administered.

The antifungal properties are most effectively utilized when Compound I is formulated into antifungal treating compositions with a biologically inert carrier which in cases of use in pharmaceutical applications should also be pharmaceutically acceptable.

The compositions are formulated according to conventional compounding techniques with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in or on inanimate objects.

The novel compositions preferably contain 5 percent or more by weight of the active compound and, if a concentrate composition, may contain 15 percent or more. In preparing the compositions, Compound I is intimately admixed with an appropriate carrier.

For non-therapeutic applications, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

For therapeutic applications, the product of the present invention may be employed in compositions employing a carrier suitable for therapeutic application. Such carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, kaolin, talc, lactose, lubricants such as calcium stearate, binders, disintegrating agents and the like.

Compound I may be used in topical application. For such applications, the drug may be formulated in conventional creams and ointments such as white petrolatum, anhydrous lanolin, cetyl alcohol, cold cream, glyceryl monostearate, rose water and the like. Usually a 5 percent cream or solution is prepared and applied to the area to be treated.

The antifungal compositions may be employed by applying to the area where fungal control is desired in such amounts as necessary to effect the desired control.

The following examples illustrate the invention but are not to be construed as limiting.

EXAMPLE I

In separate operations seed cultures were prepared by inoculating a preserved culture of the following organisms maintained in the Merck Culture Collection at Rahway, N.J. (a) *Bacillus sphaericus* MB847, (b) *Pseudomonas pseudoalcaligenes*, MB1225 and (c) *Arthrobacter simplex*, MB255 into 50 milliters of Seed Medium A and the medium incubated with shaking at 27° C. for 24 hours. At the end of this period, 2.5 milliliters of the seed culture and 5 milligrams of Compound A in 430 microliters of dimethyl sulfoxide (DMSO) were inoculated into 50 milliliters of transformation Medium A and the resulting flasks inoculated at 27° C. on a rotary shaker for 24 hours. At this time samples of the broth were assayed by HPLC using Whatman "Partisil" column (4.6×24 cm) with 46% aqueous acetonitrile for developing and the retention times compared with the starting material. It was found that each of the foregoing organisms had successfully converted the starting material to a product which has subsequently been identified as Compound I.

EXAMPLE II

A seed culture was prepared by inoculating a preserved culture of *Bacillus sphaericus* MB847, ATCC 7055 into 50 milliliters of Seed Medium A in a 250 milliliter 3-baffle Erlenmeyer flask and the flask incubated on a rotary shaker (220 rpm) at 27° C. for 24 hours. At the end of this period 10 milliliters of the seed culture and a solution of 5 milligrams of Compound A in 430 $\mu$l of DMSO were inoculated into transformation flasks containing 50 milliliters of Transformation Medium A and the resulting flasks incubated at 27° C. on a rotary shaker for 24 hours.

At the end of this period the broth was filtered and the filtered broth amounting to 150 milliliters was extracted with four 75 milliliter portions of methyl ethyl ketone. The methyl ethyl ketone layers were combined and dried over sodium sulfate, then evaporated to dryness. The residue was redissolved in 4 milliliters of methanol and further purified by high performance liquid chromatography on a Whatman "Partisil" 10 ODS-3 column (9.6×25 cm). The column was developed with 46% aqueous acetonitrile. The fractions having a retention time of 12.07 were pooled and solvent evaporated to obtain 1.76 grams of Compound I.

EXAMPLE III

In an operation carried out is a manner similar to that described in Example II, a seed culture is prepared by inoculating a preserved culture of *Pseudomonas pseudoalcaligenes* MB1225, ATCC 12815, into 50 milliliters of Seed Medium A and the medium incubated with shaking at 27° C. for 24 hours. As the end of this period, 10 milliliters of the seed culture is inoculated into transformation Medium A containing 5 milligrams of Compound A and the inoculated flask incubated at 27° C. on a rotary shaker. From time to time, the cultivation medium is checked for extent of conversion by determining the retention time of the sample on HPLC and comparing the retention time with that of Compound I produced by *B. sphaericus* as described in Example II.

EXAMPLE IV 1000 compressed tablets each containing 500 mg of Compound I are prepared from the following formulation:

| Compound | Grams |
|---|---|
| Compound I | 500 |

-continued

| Compound | Grams |
|---|---|
| Starch | 750 |
| Dibasic calcium phosphate hydrous | 5000 |
| Calcium stearate | 2.5 |

The finely powdered ingredients are mixed well and granulated with 10% starch paste. The granulation is dried and compresses into tablets.

EXAMPLE V 1000 hard gelatin capsules, each containing 500 mg of Compound I are prepared from the following formulation:

| Compound | Grams |
|---|---|
| Compound I | 500 |
| Starch | 750 |
| Dibasic calcium phosphate hydrous | 5000 |
| Calcium stearate | 2.5 |

A uniform mixture of the ingredients is prepared by blending and used to fill two-piece hard gelatin capsules.

EXAMPLE VI 250 ml of an injectable solution are prepared by conventional procedures having the following formulation:

| | |
|---|---|
| Dextrose | 12.5 g |
| Water | 250 mL |
| Compound I | 400 mg |

The ingredients are blended and thereafter sterilized for use.

EXAMPLE VII

An aerosol composition may be prepared having the following formulation:

| | Per Canister |
|---|---|
| Compound I | 24 mg |
| Lecithin NF Liquid Concentrated | 1.2 mg |
| Trichlorofluoromethane, NF | 4.026 g |
| Dichlorodifluoromethane, NF | 12.15 g |

What is claimed is:

1. A compound having the formula

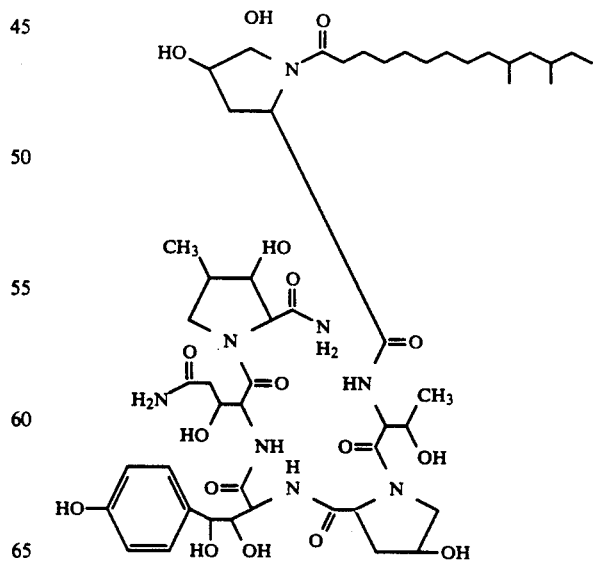

2. A composition comprising an antifungally effective amount of the compound of claim 1 in admixture with a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6
( B ) TYPE: AMINO ACID
( C ) STRANDEDNESS: Not Relevant
( D ) TOPOLOGY: LINEAR ( i i ) MOLECULE TYPE:
( A ) DESCRIPTION: PEPTIDE (iii) HYPOTHETICAL: NO (iv) ANTI-SENSE:

(v) FRAGMENT TYPE: NOT KNOWN (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO: 1:

Xaa Thr Xaa Xaa Xaa Xaa
1               5

(2) INFORMATION FOR SEQ ID NO:2:

(i) SEQUENCE CHARACTERISTICS:
    (A) LENGTH: 6
    (B) TYPE: AMINO ACID
    (C) STRANDEDNESS: Not Relevant
    (D) TOPOLOGY: CYCLIC (ii) MOLECULE TYPE:
    (A) DESCRIPTION: PEPTIDE (iii) HYPOTHETICAL: NO (iv) ANTI-SENSE:

(v) FRAGMENT TYPE: NOT KNOWN (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO: 2:

Xaa Thr Xaa Xaa Xaa Xaa
1               5